United States Patent [19]

Pigiet

[11] Patent Number: 5,028,419

[45] Date of Patent: * Jul. 2, 1991

[54] USE OF THIOREDOXIN, THIOREDOXIN-DERIVED, OR THIOREDOXIN-LIKE DITHIOL PEPTIDES IN HAIR CARE PREPARATIONS

[75] Inventor: Vincent P. Pigiet, Neshanic Station, N.J.

[73] Assignee: Repligen Corporation, Cambridge, Mass.

[*] Notice: The portion of the term of this patent subsequent to Apr. 24, 2007 has been disclaimed.

[21] Appl. No.: 397,802

[22] Filed: Aug. 23, 1989

Related U.S. Application Data

[60] Division of Ser. No. 140,353, Jan. 4, 1988, Pat. No. 4,894,223, which is a continuation-in-part of Ser. No. 770,498, Aug. 28, 1985, Pat. No. 4,919,924, which is a continuation-in-part of Ser. No. 674,893, Nov. 26, 1984, abandoned.

[51] Int. Cl.$^5$ .............................................. A61K 7/09
[52] U.S. Cl. .......................................... 424/71; 424/72
[58] Field of Search ..................................... 424/71, 72

[56] References Cited

U.S. PATENT DOCUMENTS

| | | | |
|---|---|---|---|
| 4,738,841 | 4/1988 | Pigiet | 424/71 X |
| 4,812,307 | 3/1989 | Suita-Mangzno | 424/72 X |
| 4,853,215 | 8/1989 | Brockway | 424/71 |
| 4,894,223 | 1/1990 | Pigiet | 424/72 X |
| 4,919,924 | 4/1990 | Pigiet | 424/72 |
| 4,935,231 | 6/1990 | Pigiet | 424/71 |

*Primary Examiner*—Thurman K. Page
*Assistant Examiner*—Susan S. Rucker
*Attorney, Agent, or Firm*—Saliwanchik & Saliwanchik

[57] ABSTRACT

The subject invention enables a more efficient management of hair by providing a novel preparation for waving, straightening, softening, or removing hair, employing as a key ingredient the compound thioredoxin or a thioredoxin-derived, or thioredoxin-like, dithiol peptide in combination with a sulfite or bisulfite compound.

11 Claims, No Drawings

USE OF THIOREDOXIN, THIOREDOXIN-DERIVED, OR THIOREDOXIN-LIKE DITHIOL PEPTIDES IN HAIR CARE PREPARATIONS

CROSS REFERENCE TO RELATED APPLICATIONS

This is a division of application Ser. No. 140,353 filed Jan. 4, 1988, now U.S. Pat. No. 4,894,223, which is a continuation-in-part of my co-pending application Ser. No. 770,498; filed Aug. 28, 1985 now U.S. Pat. No. 4,919,924 which is a continuation-in-part of Ser. No. 674,893, filed Nov. 26, 1984, now abandoned.

BACKGROUND OF THE INVENTION

The care of hair has been of utmost importance to mankind from the beginning of recorded history. The reign of Queen Elizabeth (1558-1603) became noted for its attention to the finer aspects of hair styling; it was Her Majesty who set the standard. During this Elizabethan period, hair was arranged in elaborate high coiffures, and curled and frizzed by whatever means were available. Needless to say, as measured by present day available hair care products and methods, the Elizabethan hair care procedures were primitive, at best. The discovery of new chemicals and properties thereof led to the beginning of hair care products designed to beautify and maintain the hair in a healthy, youthful state. These desirable human hair properties were achieved by use of a variety of hair care products, including hair dyes and products used to impart a wave to the hair. Wavy hair is considered a desirable human hair feature, whereas straight hair is usually held in less favor. Because of these human demands to beautify the hair, there has evolved a multitude of hair care products with a variety of claims and promises. With hair care products designed to dye or wave the hair, it has been found that the structure of the hair shaft itself must be reckoned with in order to have a product which would give the desired results. A key detail of the hair shaft, which is predominantly keratinaceous in nature, is that the keratin fibers are bonded together by disulfide cross-linkages. It is this detail of the hair structure which the subject invention is concerned with. The prior art discloses the severance of the disulfide crosslink with, enter alia, various chemical agents.

In a normal 'tepid' waving process, keratin disulfides are reduced by use of either sulfites or bisulfites. Sulfite and bisulfite waving have the advantage of being less damaging than a thioglycolate wave with less likelihood of overprocessing. Drawbacks to the sulfite and bisulfite waving process however, are that they give soft waves and the permanent does not last as long as the thioglycolate wave. An additional detraction of the bisulfite wave is the formation of keratin thiosulfates, commonly known as Bunte salts. The presence of residual Bunte salts can lead to relaxation of the curl through disulfide exchange and to lanthionine formation causing irreversible hair damage. These Bunte salts can also affect the texture and feel of hair.

BRIEF SUMMARY OF THE INVENTION

The subject invention concerns the surprising and advantageous discovery that the use of sulfite or bisulfite compounds in hair care preparations can be dramatically improved upon by use of thioredoxin or a thioredoxin-derived, or thioredoxin-like, dithiol peptide compounds. This combination gives rise to a synergistic effect in terms of efficiently breaking the disulfide bond of hair keratin. The net result is that significantly lesser amounts of sulfite or bisulfite compounds are needed to produce the desired effect in the hair. Coupled with this reduction of sulfite or bisulfite compounds use are other desirable features: The hair can be waved in a shorter time and Bunte salts formed can be cleaved from the hair fiber. In achieving these desirable results, the subject invention enhances rather than compromises the reductive properties of sulfite or bisulfite compounds and additive dithiol peptides.

DETAILED DISCLOSURE OF THE INVENTION

Upon adding thioredoxin or a thioredoxin-derived, or thioredoxin-like, dithiol peptide to a hair care product containing a bisulfite or sulfite compound, e.g., a hair preparation for straightening, waving, removing, or softening hair, there is realized a synergistic effect whereby significantly lesser amounts of sulfite or bisulfite compound are needed to produce the desired effect. For example, in commercial practice, sodium or ammonium bisulfite is used in waving lotions at about 7.0% concentration levels. As the bisulfite concentration increases from about 0.01% to about 7.0%, the amount of hair curling increases with a leveling off occurring at about 7.0%. By adding thioredoxin or a thioredoxin-derived, or thioredoxin-like, dithiol peptide to the waving preparation, the bisulfite concentration can be reduced by a factor of two to about 3.2% and still give the same amount of waving as a commercial waving lotion containing 7.0% bisulfite.

The concentration of thioredoxin or one of the thioredoxin-derived, or thioredoxin-like, dithiol peptides which can be used to enhance the effect of a sulfite or bisulfite compound ranges from about 1 to about 100 nmole/ml. The optimal concentration for intact bacterial thioredoxin appears to be about 2 nmole/ml. It should be recognized that the precise level of thioredoxin or thioredoxin-derived, or thioredoxin-like, dithiol peptide in combination with a sulfite of bisulfite compound can be readily ascertained for a particular hair sample by a person skilled in the hair care art having possession of the subject invention.

Thioredoxins are low molecular weight dithiol proteins that have the ability to reduce disulfides in typical organic compounds such as Ellman's reagent or disulfides as they exist naturally in a variety of proteins (Holmgren, A. [1981] Trends in Biochemical Science 6:26-39). Thioredoxin and thioredoxin-derived, or thioredoxinlike, dithiol peptides within the scope of the subject invention are exemplified by the following compounds: (1) thioredoxin isolated from *Escherichia coli* (Laurent, T. C., Moore, E. C., and Reichard, P. [1964] J. Biol. Chem. 239:3436-3445);

(2) thioredoxins isolated from other sources, e.g., thioredoxin isolated from yeast (Porque, G. P., Baldesten, A., and Reichard, P. [1970] J. Biol. Chem. 245:2362-2379); Cyanobacterium (Gleason, F. K. and Holmgren, A. [1983] in "Thioredoxins, Structure and Function" [P. Gadal, ed.] Editions du Centre National de la Recherche Scientifique); rat (Guerara, J., Moore, E. C., and Ward, D. NM. [1983] ibid); T₄ bacteriophage (Soderberg, B. O. Sjoberg, B.-M., Sonnerstam, U., and Branden, C-I. [1978] Proc. Natl. Acad. Sci. USA 75:5827-5830); purification of mammalian thioredoxin (Luthman, M. and Holmgren, A. [1982] Biochem.

121:6628-6633); further, thioredoxin from a human source can be used in the subject invention;

(3) thioredoxin-derived dithiol peptides representing peptides produced by cleavage of intact thioredoxins, as described infra. One such example of this class of thioredoxin-derived peptides is the fragment containing residues 1 through 37 (i.e., $T_{1-37}$) produced by cyanogen bromide cleavage of thioredoxin from *E. coli*.

The important feature of these thioredoxin derived dithiol peptides is that they contain the redox-active peptide sequence, Cys-X-Y-Cys, wherein X and Y, independently, can be any of the natural 20 amino acids. For example, the redox-active peptide sequence from *E. coli* thioredoxin is Cys-Gly-Pro-Cys (Cys=cysteine, Gly=glycine, Pro=proline). Also the redox-active sequences Cys-X-Y-Cys-Lys or Trp-Cys-X-Y-Cys-Lys, wherein X and Y are as defined above, for example, Cys-Gly-Pro-Cys-Lys or Trp-Cys-Gly-Pro-Cys-Lys can be used; and (4) thioredoxin-like dithiol peptides that inter alia have the intrinsic ability to catalyze the reduction of protein disulfides. These thioredoxin-like dithiol peptides will generally have the characteristic of containing a pair of cysteine residues which form a redox-active disulfide. This example includes peptides, derived from natural sources or constructed synthetically, that include the same redox-active sequence as disclosed above, for example in *E. coli* thioredoxin, Cys-Gly-Pro-Cys, Cys-Gly-Pro-Cys-Lys, or Trp-Cys-Gly-Pro-Cys-Lys, or analogous sequences from other thioredoxins such as that encoded for by T4 bacteriophage, Cys-Val-Tyr-Cys (Cys=cysteine, Val=valine, Tyr=tyrosine) (Soderberg, B.-O., Sjoberg, B.-M., Sonnerstam, U., and Branden, C.-I. [1978] Proc. Natl. Acad. Sci. USA 75:5827-5830). Other thioredoxin-like peptides include the class of seed proteins called purothionins that have intrinsic thioredoxin-like activity (Wada, K. and Buchanan, B. B. [1983] in "Thioredoxins, Structure and Function" [Gadal, P., ed.]Editions du Centre National de la Recherche Scientifique).

Following are examples which illustrate products of the invention and procedures, including the best mode, for practicing the invention. These examples should not be construed as limiting. All percentages are by weight and all solvent mixture proportions are by volume unless otherwise noted.

EXAMPLE 1

Bisulfite Waving Solutions

The bisulfite waving solution consisted of 7% (w/w) ammonium bisulfite, 4.65% (w/w) ethanol, and 0.6% (w/w) polyoxyethylene(23) lauryl ether. The pH was adjusted to 7.5 with ammonium hydroxide. All dilutions of the 7% solution were made using a diluent consisting of all components except the ammonium bisulfite. The neutralizer contained 2.3% hydrogen peroxide adjusted to pH 3.3 with dilute phosphoric acid. All solutions were overlayed with argon or nitrogen and stored in the dark at room temperature for up to 2 months.

Hair Waving Assay

The influence of thioredoxin and active site peptides on bisulfite permanent waving was determined by direct hair waving assays. Tresses were divided into smaller tresses approximately 0.5 cm wide and 12 to 13 cm in length. Each tress weighed approximately 0.2 g.

Intact tresses were shampooed before waving with SILKIENCE TM for normal hair (The Gillette Company, Boston, Mass.). Each tress was shampooed and thoroughly rinsed two times before being combed through and allowed to air dry. Bleached-waved tresses were used as received with no additional treatment.

Each tress was treated with a total of 3 ml of waving lotion. Half the lotion (1.5 ml) was applied to the tress and the saturated tress remained at room temperature for 20 minutes before being combed through and rolled. An end paper was folded around the tress to assure that the tress was flat and all ends were covered. The tress was rolled firmly and evenly on the medium orange rods (0.6–0.7 mm diameter) available in the RAVE TM curler assortment (Chesbrough-Pond's Inc., Trumbull, Conn.). After the tress was rolled it remained at room temperature for an additional 20 minutes. The tress was then saturated with the remaining waving lotion, covered with plastic wrap, and incubated for 60 minutes at 33°–34° C. After 60 minutes the tress was rinsed for 3 minutes with 40° C. tap water, blotted dry, and neutralized.

The tress was saturated with neutralizer and resaturated after 90 seconds. After 10 minutes at room temperature, the rod was removed from the tress and the neutralizer worked down to the end of the tress. After an additional 2 minutes the tress was rinsed for 2 minutes with 40° C. tap water and the hanging length was measured immediately while the tress was wet.

Differences in the amount of waving from the different solutions were quantitated by measuring the hanging length before and after waving. The relative hair length was calculated according to the following equation:

$$RHL = \frac{L_a}{L_b}$$

where RHL is the relative hair length, $L_b$ the length before waving, and $L_a$ the length after waving.

EXAMPLE 2

Influence of Thioredoxin

Thioredoxin was effective in increasing the waving obtained from a bisulfite solution in hair. As anticipated, the amount of waving with bisulfite alone was significantly less in intact hair (RHL=0.74) as compared to bleached-waved hair (RHL 0.70). The increase in waving with the addition of thioredoxin was also more significant. The RHL with the addition of thioredoxin was 0.69 for intact hair compared to 0.68 for bleached-waved hair. Thioredoxin in 3.2% bisulfite produced more waving than a 7% commercial preparation (CLAIROL KINDNESS TM ). The amount of dithiol required to give the maximal effect was 2–5 µM.

The addition of thioredoxin affected the processing time required in treated hair. The presence of thioredoxin significantly reduces the observed biphasic nature of the reaction. For example, in intact hair, thioredoxin increased the amount of waving at a reaction time as short as 15 minutes. Intact tresses were waved with a 3.2% bisulfite solution alone or containing 5 µM thioredoxin. As with treated hair, the greatest increase in waving with the addition of thioredoxin was at 45 minutes.

These results indicate two important conclusions. First, with the addition of thioredoxin the amount of waving in a bisulfite system can be increased. Second, if no increase in the amount of waving is desired, the processing time can be reduced from 60 minutes to 40-45 minutes with the addition of thioredoxin to a 3.2% bisulfite solution.

EXAMPLE 3

Influence of Thioredoxin and Cysteine Methyl Ester

Studies on the cleavage of a model Bunte salt with thioredoxin supported the idea that at low pH a stable sulfonated thioredoxin intermediate is formed and this intermediate could be recycled to reduced thioredoxin by the addition of a secondary reductant such as cysteine methyl ester or cysteine. Above neutral pH this intermediate is unstable and oxidized thioredoxin is formed.

The effect of reduced thioredoxin (5 $\mu$M) and various concentrations of cysteine methyl ester on permanent waving at neutral pH was determined. Cysteine methyl ester in the absence of thioredoxin increased the amount of waving though it was not as effective as intact thioredoxin. The presence of cysteine methyl ester had no effect on waving with intact thioredoxin.

Waving obtained with reduced thioredoxin in the absence of cysteine methyl ester was comparable to that using oxidized thioredoxin. Since the reduced form of the enzyme is necessary to cleave Bunte salts, this shows that thioredoxin may be involved in something other that Bunte salt cleavage when added directly to the bisulfite waving solution. The other possibility is that thioredoxin is reduced by the bisulfite and then cleaves Bunte salts.

EXAMPLE 4

Influence of $T_{31-36}$ and Cysteine

The effect of a secondary reductant with $T_{31-36}$ (trp-Cys-Gly-Pro-Cys-Lys) was studied to determine whether the amount of waving obtained with the minimal peptide could be increased. $T_{31-36}$ is one of the minimal active site peptides and is not limited by molecular size as is intact thioredoxin. Cysteine was used as the secondary reductant in the presence of reduced $T_{31-36}$ (2 $\mu$M) and 3.5% bisulfite. Cysteine itself gave increased waving in the $\mu$M range. However, the presence of both $T31\mp$and cysteine (10 $\mu$M) in bisulfite showed no increase in waving as compared to bisulfite alone.

Preparation of Thioredoxin Compounds

Production of Purified Thioredoxin

Thioredoxin is purified either from a commercial source of *E. coli*, strain B (Grain Processing Corp., Minneapolis, Minn.) or from any of a number of strains of *E. coli* grown by standard procedures (Pigiet, V. and Conley, R. R. [1977] J. Biol Chem. 252:6367–6372). The protein is purified using standard procedures including chromatography on ion exchange and molecular sieve columns (Williams, C. H., Zanetti, G., Arscott, L. D., and McAllister, J. K. [1967] J. Biol. Chem. 242:5226–5231; and McEvoy, M., Lantz, C., Lunn, C. A., and Pigiet, V. [1981]J. Biol Chem. 256:6646–6650). Thioredoxin was at least 95% homogeneous as determined by SDS-polyacrylamide gel electrophoresis. The enzyme was stored in 5 ml aliquots in −20° C. in 0.05M Tris, pH 7.4 with 1 mM EDTA.

Assay for thioredoxin

Thioredoxin protein was assayed immunologically using quantitative rocket immunoelectrophoresis as described previously (McEvoy, M., Lantz, C., Lunn, C. A., and Pigiet, V. [1981] J. Biol. Chem. 256:6646–6650).

Isolation of $T_{1-37}$ $T_{1-37}$ was produced by cyanogen bromide cleavage of thioredoxin. A sample of thioredoxin was dialyzed in water for 12 hr. at 4° C. The sample was taken to dryness and resuspended in 70% formic acid and added to thioredoxin in a 50-fold molar excess. The solution was purged with nitrogen and incubated at room temperature in the dark for at least 24 hr. At the completion of the cleavage reaction the solution was dried under nitrogen and resuspended in a minimal amount of concentrated ammonium hydroxide. When the sample was dissolved, the pH of the sample was adjusted to 8.0 with concentrated HCl. The sample was stored at −20° C. under argon and aliquots were removed for purification.

$T_{1-37}$ was isolated by affinity chromatography on thiopropyl sepharose 6B. A sample of the CNBr digest was incubated with a 2-fold molar excess of DTT for 10 minutes at room temperature before being applied to a thiopropyl column equilibrated with 0.1 M Tris, pH 7.5, containing 0.5M NaCl and 1 mM EDTA. The column was washed with two column volumes of the equilibrating buffer containing 2M urea to remove any $T_{38-108}$ that was non-specifically bound. The column was then washed with an additional 2 column volumes of equilibrating buffer. $T_{1-37}$ was eluted from the column with 25mM DTT in equilibrating buffer. The sample was analyzed for homogeneity by reverse phase high pressure liquid chromatography on a Waters $\mu$-Bondpak $C_{18}$ column attached to a Beckman Model 421 system monitored at 214 nm.

A 0–60% gradient of acetonitrile containing 0.08 to 0.1% TFA was used to elute the peptide at a flow rate of 2 ml/min. The peptide was judged to be greater than 95% pure by this procedure.

DTT was removed from the sample by exclusion chromatography. The sample volume was reduced using a Savant Speed Vac Concentrator and applied to a 1 cm×25 cm column of Sephadex TM G-25-40 equilibrated with 0.05M Tris, 1 mM EDTA, pH 7.4 (TE buffer). The 0.3 ml fractions collected were monitored at 280 nm. The samples containing $T_{1-37}$ were pooled and the concentration determined by $A_{280}$ (280=10,000 cm$^{-1}$M$^{-1}$). The sample was immediately used in the waving assay.

Isolation of $T_{32-37}$ $T_{32-37}$ was isolated from a chymotryptic digest of the CNBr digest. Chymotrypsin was added to a prewarmed (37° C.) solution of CNBr digest to a final concentration of 1:20 (w/w) chymotrypsin to peptide. After incubating the sample for 1 hr L-1-Tosylamide-2-phenylethylchloromethyl ketone (TPCK) was added in a 1:1 molar ratio to chymotrypsin to stop the reaction.

The sample was loaded onto a Waters $\mu$-Bondpak $C_{18}$ column attached to a Beckman Model 421 system monitored at 214 nm. The solvent system employed was 0.1% trifluoroacetic acid (Buffer A) and 0.08% trifluoroacetic acid in acetonitrile (Buffer B). A gradient from 0–30% B over 30 minutes and 30–60% over 15 minutes was used to separate the peptides at a flow rate of 2 ml/min. The peak identified as $T_{32-37}$ was collected, taken to dryness, and stored under argon at $-20°$ C.

Reduction of $T_{31-36}$ $T_{31-36}$ was obtained synthetically and was reduced for several experiments. The peptide was incubated at 37° C. for 1 hr with a 5-fold molar excess of DTT. The DTT was removed by HPLC as described for the isolation of $T_{32-37}$. $T_{31-36}$ was taken to dryness, reconstituted with a minimal volume of TE buffer and used immediately in the waving assay. The procedure was only partially effective, with only 30% of the peptide reduced as determined by cleavage of a model Bunte salt.

I claim:

1. A composition of matter for waving or straightening human hair which comprises a sulfite or bisulfite compound and thioredoxin-derived, dithiol peptide wherein said sulfite or bisulfite compound is present at a concentration of about 0.1M to about 1.0M, and said thioredoxin or thioredoxin-derived, dithiol peptide is present at a concentration of about 0.1 μmole/ml to about 100 μmole/ml.

2. A composition of matter for waving human hair, according to claim 1, wherein said thioredoxin-derived dithiol peptide is the fragment containing residues 1 through 37 produced by cyanogen bromide cleavage of *E. coli* thioredoxin.

3. A composition of matter for waving human hair, according to claim 1, wherein said thioredoxin-derived dithiol peptide is the fragment containing residues 19–36 produced by trypsin digestion of residues 1 through 37 produced by cyanogen bromide cleavage of *E. coli* thioredoxin.

4. A process for waving or straightening human hair which comprises applying to said human hair a composition comprising a sulfite or bisulfite compound and thioredoxin-derived, dithiol peptide wherein said sulfite or bisulfite compound is present at a concentration of about 0.1 M to about 1.0M, and said thioredoxin-derived dithiol peptide is present at a concentration of about 0.1 μM mole/ml to about 100 μmole/ml.

5. A process for waving human hair, according to claim 4, wherein said sulfite or bisulfite compound is present at a concentration of about 0.1M to about 1.0M, and said thioredoxin or thioredoxin-derived, dithiol peptide is present at a concentration of about 1 nmole/ml to about 100 nmole/ml.

6. A process for waving human hair, according to claim 4, wherein said thioredoxin-derived, dithiol peptide is the fragment containing residues 1 through 37 produced by cyanogen bromide cleavage of *E. coli* thioredoxin.

7. A process for waving human hair, according to claim 4, wherein said thioredoxin-derived, dithiol peptide is the fragment containing residues 19 through 36 produced by trypsin digestion of residues 1 through 37 produced by cyanogen bromide cleavage of *E. coli* thioredoxin.

8. A process, according to claim 4, wherein said thioredoxin-derived, dithiol peptide comprises the redox-active peptide sequence Cys-X-Y-Cys, Cys-X-Y-Cys-Lys, or Trp-Cys-X-Y-Cys-Lys, wherein X and Y, independently, can be any of the natural 20 amino acids.

9. A process, according to claim 8, wherein said redox active peptide sequence is Cys-Gly-Pro-Cys, or Cys-Gly-Pro-Cys-Lys, or Trp-Cys-Gly-Pro-Cys-Lys.

10. A composition of matter for straightening hair, according to claim 1, which comprises a sulfite or bisulfite compound and thioredoxin or a thioredoxin-derived, dithiol peptide.

11. A process for waving or straightening animal hair which comprises applying to said animal hair a composition comprising a sulfite or bisulfite compound and thioredoxin or thioredoxin-derived, dithiol peptide wherein said sulfite or bisulfite compound is present at a concentration of about 0.1M to about 1.0M, and said thioredoxin or thioredoxin-derived, dithiol peptide is present at a concentration of about 0.1 μmole/ml to about 100 μmole/ml.

* * * * *

UNITED STATES PATENT AND TRADEMARK OFFICE
CERTIFICATE OF CORRECTION

PATENT NO.    :  5,028,419

DATED         :  July 2, 1991

INVENTOR(S)   :  Vincent P. Pigiet

It is certified that error appears in the above-identified patent and that said Letters Patent is hereby corrected as shown below:

| | | |
|---|---|---|
| Column 7: | line 18: | After "compound and" insert --thioredoxin or a--. |
| Column 7: | line 39: | Before "thioredoxin-derived" insert -- thioredoxin or a--. |
| Column 7: | line 41: | After "1.0M, and said" insert --thioredoxin or--. |

Signed and Sealed this

First Day of December, 1992

*Attest:*

DOUGLAS B. COMER

*Attesting Officer*    Acting Commissioner of Patents and Trademarks